US00PP28836P2

(12) United States Plant Patent
Wood

(10) Patent No.: US PP28,836 P2
(45) Date of Patent: Jan. 2, 2018

(54) ***BUDDLEIA* PLANT NAMED 'SMNBDPT'**

(50) Latin Name: *Buddleia davidii*
Varietal Denomination: SMNBDPT

(71) Applicant: Timothy Wood, Spring Lake, MI (US)

(72) Inventor: Timothy Wood, Spring Lake, MI (US)

(73) Assignee: Spring Meadow Nursery, Inc, Grand Haven, MI (US)

( * ) Notice: Subject to any disclaimer, the term of this patent is extended or adjusted under 35 U.S.C. 154(b) by 0 days.

(21) Appl. No.: 15/330,700

(22) Filed: Oct. 28, 2016

(51) Int. Cl.
*A01H 5/00* (2006.01)

(52) U.S. Cl.
USPC ..... Plt./242

(58) Field of Classification Search
USPC ..... Plt./242
CPC ..... A01H 5/00; A01H 5/02
See application file for complete search history.

*Primary Examiner* — Kent L Bell
(74) *Attorney, Agent, or Firm* — Cassandra Bright

(57) ABSTRACT

A new and distinct *Buddleia* cultivar named 'SMNBDPT' is disclosed, characterized by compact, dense habit less than 2 feet tall with thick, chunky stems with short internodes; heavy, wide, coriaceous, textured leaves; large and wide panicles of purple flowers; and cold hardiness. The new variety is a *Buddleia*, normally produced as an outdoor garden or container plant.

2 Drawing Sheets

Figure 1:
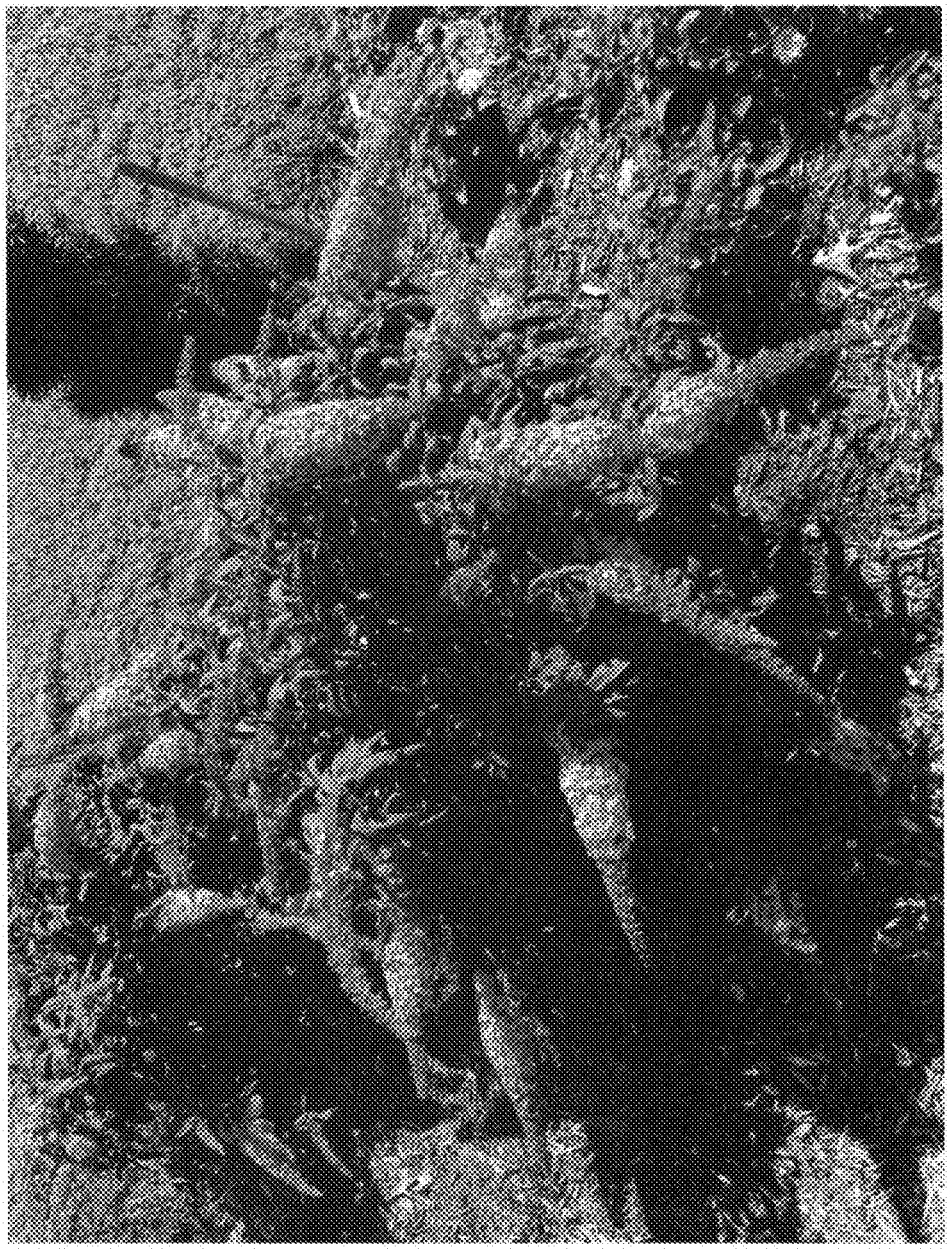

Latin name of the genus and species: *Buddleia davidii*.
Variety denomination: 'SMNBDPT'.

BACKGROUND OF THE INVENTION

The new *Buddleia* cultivar is a product of a planned breeding program conducted by the inventor, Timothy D. Wood, in Grand Haven, Mich., USA. The objective of the breeding program was to produce compact plants with strong branches in a range of flower colors. The cross resulting in this new variety was made during 2012.

The seed parent is the unpatented *Buddleia davidii* 'UC 596'. The pollen parent is the unpatented *Buddleia davidii* 'Adonis Blue'. The new variety was discovered in 2013 by the inventor in a group of seedlings resulting from the 2012 crossing, in Grand Haven, Mich., USA.

Asexual reproduction of the new cultivar was performed by softwood stem cuttings. This was first performed in Grand Haven, Mich., USA in 2013 and has shown that the unique features of this cultivar are stable and reproduced true to type in 6 successive generations.

SUMMARY OF THE INVENTION

The cultivar 'SMNBDPT' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMNBDPT' These characteristics in combination distinguish 'SMNBDPT' as a new and distinct *Buddleia* cultivar:

1. Compact, dense plants less than two feet tall. Spreading and somewhat flat-topped habit.
2. Thick, chunky stems with short internodes.
3. Heavy, wide, coriaceous, textured leaves.
4. Large and wide panicles of purple flowers.

5. Cold hardiness comparable to the most cold-hardy *Buddleia davidii* on the market.

PARENT COMPARISON

Plants of the new cultivar 'SMNBDPT' are similar to plants of the seed parent in most horticultural characteristics, however, plants of the new cultivar 'SMNBDPT' differ in the following;

1. The cultivar grows to a larger plant than the seed parent.
2. The new variety has larger flowers than the seed parent.
3. The new variety has purple flowers, whereas the seed parent has purple-blue flowers.

Plants of the new cultivar 'SMNBDPT' are similar to plants of the pollen parent in most horticultural characteristics, however, plants of the new cultivar 'SMNBDPT' differ in the following;

1. The new variety is shorter than the pollen parent.
2. The new variety has purple flower, the pollen parent has deep blue flowers.
3. The new variety has larger flowers than the pollen parent.
4. The new variety has wider leaves than the pollen parent.

COMMERCIAL COMPARISON

Plants of the new cultivar 'SMNBDPT' are comparable to the patented commercial variety *Buddleia* 'Purple Haze', U.S. Plant Pat. No. 24,514. The two *Buddleia* varieties are similar in most horticultural characteristics; however, the new variety 'SMNBDPT' differs in the following:

1. The new cultivar has upright facing flowers, the comparator has flowers somewhat downward.
2. The new cultivar has tighter flower clusters, whereas the comparator has looser flower clusters.
3. The new cultivar has darker, more purple colored flowers than this comparator.

4. The new variety growth habit is compact and rounded, this comparator has a growth habit which is compact and spreading.

Plants of the new cultivar 'SMNBDPT' are comparable to the variety *Buddleia* 'SMNBDBT', co-pending U.S. Plant patent application Ser. No. 15/330,699. The varieties differ from each other primarily in flower color.

BRIEF DESCRIPTION OF THE PHOTOGRAPHS

The accompanying photograph in FIG. 1 illustrates a plant of 'SMNBDPT' grown in the ground.

Figure 2:
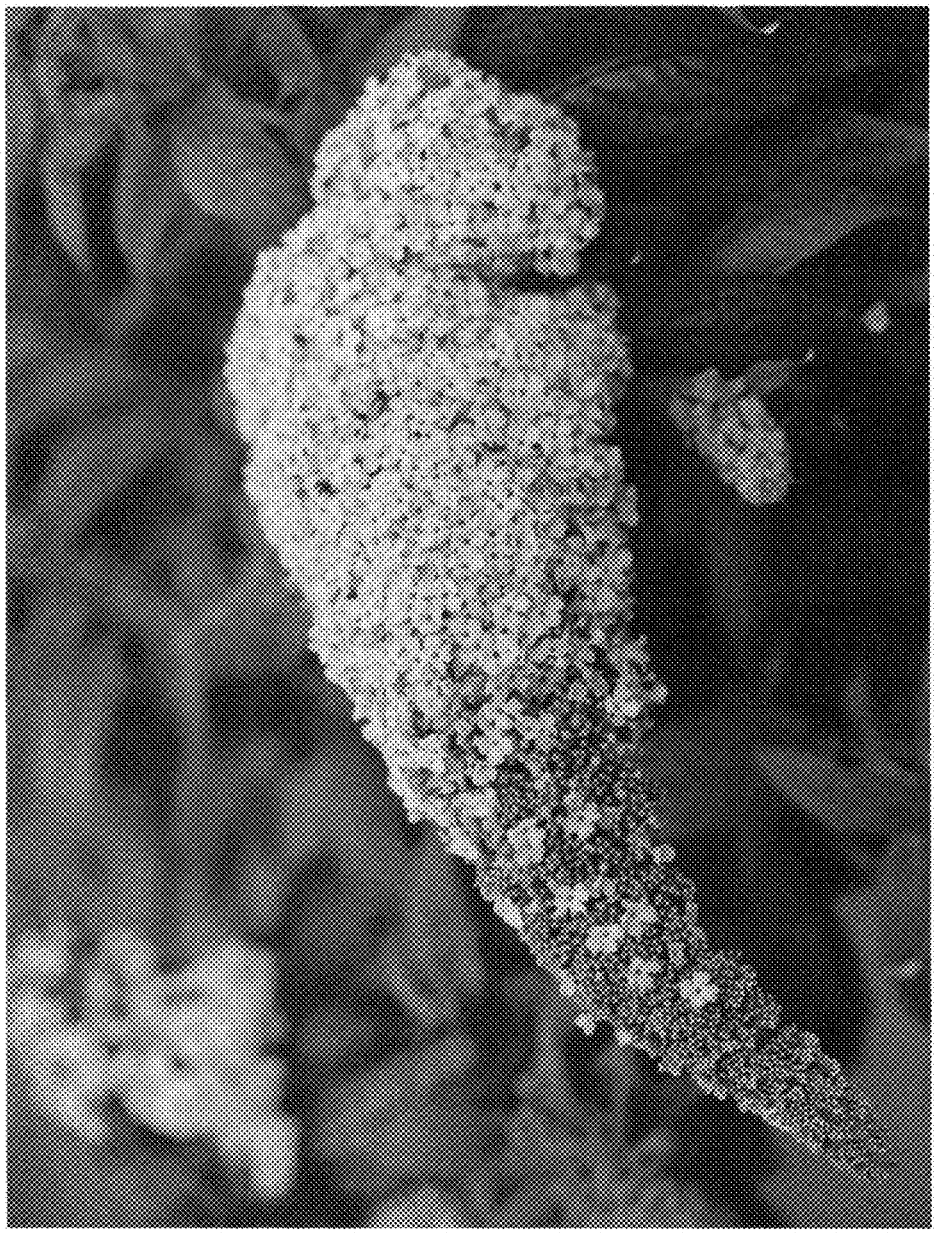

FIG. 2 illustrates in full color a typical inflorescence of 'SMNBDPT' Age of the plant photographed is approximately 2-3 years old from a rooted cutting.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 1996 except where general terms of ordinary dictionary significance are used. The following observations and measurements describe 'SMNBDPT' plants grown in a poly greenhouse during June, in Grand Haven, Mich. USA. The growing temperature ranged from 18° C. to 27° C. during the day and from 5° C. to 10° C. during the night. General light conditions are natural sunlight. Measurements and numerical values represent averages of typical plant types.

Botanical classification: *Buddleia davidii* 'SMNBDPT'.

PROPAGATION

Type of propagation typically used: Softwood cutting.

Time to initiate roots: 14-21 days at 21-29° C. average temperature.

Time to produce a rooted young plant: 30 days at 21-29° C. average temperature.

Root description: Dense, free-branching, medium thickness, fibrous. Color is white, not accurately described with R.H.S. chart.

PLANT

Age of plant described: 2-3 years from rooted cutting.

Plant type: Perennial shrub.

Container size of the plant described: In ground.

Appropriate containers: 1, 2, 3 gallon commercial pots.

Growth habit: Upright and rounded.

Height: 50 cm.

Plant spread: 105 cm.

Growth rate: Moderate.

Plant vigor: Strong.

Characteristics of primary lateral branches:

- *Quantity*.—Approximately 10.
- *Branching habit*.—Upright and slightly outward.
- *Branch appearance*.—Woody, with pubescence on newer growth. Rounded.
- *Length*.—38 to 42 cm.
- *Diameter*.—8 mm.
- *Color*.—Near RHS Yellow-Green 144B, with pubescence rubbed off, near Green 139D with pubescence. Bark near Grey-Brown 199B with striations near 199A.
- *Pubescence*.—Present, dense.
- *Stem aspect/angle*.—Approximately 0 to 35°.
- *Strength*.—Good.

Internode length: 2.5 to 3.5 cm.

FOLIAGE

Leaf:

- *Arrangement*.—Opposite, single.
- *Average length*.—14 cm.
- *Average width:* 5.2 cm.
- *Shape*.—Lanceolate.
- *Apex*.—Acute to acuminate.
- *Base*.—Cuneate.
- *Margin*.—Slightly undulate and serrate.
- *Texture of top surface*.—Soft, coriaceous, and pubescent with distinct veins.
- *Texture of bottom surface*.—Soft and pubescent with distinct veins.
- *Pubescence*.—Yes, both upper and lower side of leaf.
- *Color*.—Young foliage upper side: Near RHS Green 138A, fading to RHS Green 137A near apex. Young foliage under side: Near RHS Greyed-Green 194C. Mature foliage upper side: Near RHS Green 139A. Mature foliage under side: Near RHS Greyed-Green 191C.
- *Venation*.—Type: Pinnate. Venation color upper side: Near RHS Green 143B. Venation color under side: Near RHS Yellow-Green 145B and 145C, both colors present individually.
- *Petiole*.—Length: 1.0 to 5.0 mm. Diameter: 1.0 to 2.5 mm. Color: Upper side: Near RHS Yellow-Green 147D. Lower side: Near RHS Yellow-Green 147D. Texture: Upper side: Soft and pubescent. Lower side: Soft and pubescent.

FLOWER

Flower arrangement: Cone-shaped panicle.

Flower type: Salverform.

Flowering habit: Freely flowering on terminal branches, will develop panicles at other nodes after terminal panicle has bloomed.

Natural flowering season: Mid-summer to early fall.

Inflorescence height: Average 21.2 cm, largest 28 cm.

Inflorescence width: Average 6.9 cm, largest 8.5 cm.

Flower longevity on plant: 3-4 weeks.

Persistent or self-cleaning: Persistent.

Quantity of flowers per inflorescence: Thousands.

Quantity of flowers per plant: Thousands.

Bud:

- *Shape*.—Linear with protruding square cap.
- *Length*.—10.0 mm.
- *Diameter*.—1.5 mm.
- *Color*.—Near RHS Tip Violet 84C, mid-section Red-Purple 70C, White 155C at base.

Flower size:

- *Diameter*.—6 mm.
- *Length*.—8 mm.

Petals:

- *Appearance*.—Smooth, vibrant.
- *Arrangement*.—Whorled.

*Petal length.*—3.0 mm.
*Petal width.*—3.0 mm.
*Quantity.*—4.
*Texture.*—Smooth and soft.
*Apex.*—Obtuse.
*Shape.*—Oblong to obovate.
*Base.*—Slightly acute.
*Margin.*—Faintly undulate.

Petal color:
*When opening.*—Upper surface: Near RHS Purple 77C. Lower surface: Near RHS Purple 77C.
*Fully opened.*—Upper surface: Near RHS Purple 77C. Lower surface: Near RHS Purple 77C.
*Fading to color.*—Upper: Near RHS Greyed-Orange 165B. Lower: Near RHS Greyed-Orange 165B.

Sepals:
*Quantity per flower.*—4.
*Arrangement.*—Fused into calyx tube.
*Shape.*—Lanceolate to Ovate.
*Length.*—3.0 mm.
*Width.*—0.5 mm.
*Apex.*—Acute.
*Base.*—Cuneate.
*Margin.*—Entire.
*Texture.*—Upper: Slightly pubescent. Lower: Slightly pubescent.
*Color.*—Upper Surface: Near RHS Yellow-Green 145C fading to 147C towards apex. Lower Surface: Near RHS Yellow-Green 145C fading to 147C towards apex.

Calyx:
*Shape.*—Oblong and unguiculate.
*Length.*—3.0 mm.
*Diameter.*—1.0 mm.

Peduncle:
*Length.*—3 to 5 mm.
*Diameter.*—0.5 mm.
*Angle.*—Upright, outward.
*Strength.*—Good.
*Texture.*—Smooth, pubescent.
*Color.*—Near RHS Yellow-Green 147D.

Pedicel:
*Length.*—1 mm.
*Diameter.*—Less than 0.5 cm.
*Angle.*—Outwardly facing.
*Strength.*—Good.
*Texture.*—Smooth.
*Color.*—Near RHS Yellow-Green 147D.

Fragrance: Strong honey scent.

REPRODUCTIVE ORGANS

Stamens:
*Number.*—4.
*Filament length.*—1.0 mm.
*Filament color.*—Near RHS Greyed-Yellow 161A.

Anthers:
*Shape.*—Oblong.
*Length.*—1.0 mm.
*Color.*—Near RHS White 155B.
*Pollen.*—Quantity: Moderate. Color: Near RHS Yellow 11C.

Pistil:
*Number.*—1.
*Length.*—4.0 mm.
*Style.*—Length: 1.0 mm. Color: RHS Yellow-Green 145A.
*Stigma.*—Shape: Oblong. Color: Near RHS Yellow-Green 145A. Ovary Color: RHS Yellow-green 145A.

OTHER CHARACTERISTICS

Seeds and fruits: None observed to date.
Disease/pest resistance: Neither resistance nor susceptibility to the normal diseases and pests of *Buddleia* observed to date.
Lowest temperature tolerance: To date in trials −31° C.
Highest temperature tolerance: To date in trials 38° C.
Garden performance: Good, strong stems resist breakage from environmental stressors.

What is claimed is:

1. A new and distinct cultivar of *Buddleia davidii* plant named 'SMNBDPT' as herein illustrated and described.

* * * * *